United States Patent [19]

Loane

[11] Patent Number: 4,953,853
[45] Date of Patent: * Sep. 4, 1990

[54] SKI EXERCISING APPARATUS

[76] Inventor: R. Joel Loane, 535 Placitas Ave., Atherton, Calif. 94025

[*] Notice: The portion of the term of this patent subsequent to May 10, 2005 has been disclaimed.

[21] Appl. No.: 178,354

[22] Filed: Apr. 6, 1988

Related U.S. Application Data

[63] Continuation-in-part of Ser. No. 80,755, Jul. 30, 1987, Pat. No. 4,743,014.

[51] Int. Cl.$^5$ .............................................. A63B 69/00
[52] U.S. Cl. ...................................... 272/97; 272/142
[58] Field of Search ..................... 272/97, 142, 69, 70, 272/72, 93, 96, 146, 127, 135, 136, 138, DIG. 4; 128/25 R, 25 B; 434/253

[56] References Cited

U.S. PATENT DOCUMENTS

| | | | |
|---|---|---|---|
| 3,511,499 | 5/1970 | Schawalder | 272/97 |
| 3,524,641 | 8/1970 | Ossenkop | 272/97 |
| 3,547,434 | 12/1970 | Ossenkop | 272/97 |
| 3,704,885 | 12/1972 | Raciunas | 272/97 |
| 3,791,645 | 12/1974 | Stelma | 272/97 |
| 4,376,532 | 3/1983 | Hunstad | 272/97 |
| 4,743,014 | 10/1988 | Loane | 272/97 |

FOREIGN PATENT DOCUMENTS 2443695  3/1976  Fed. Rep. of Germany ........ 272/97

Primary Examiner—Stephen R. Crow
Attorney, Agent, or Firm—Joseph H. Smith

[57] ABSTRACT

A ski exercise device is provided having at least two parallel rails held in a fixed relationship by brace elements at the ends. A carriage is provided for riding along the rails, and a first resilient element provides a restoring force on the carriage directed toward the center of the rails. Platforms for a user's feet are pivotally attached to the carriage off-center from the centerline of the platforms so that the natural action by a user in shifting weight from one platform to the other platform in operation causes the respective platforms to pivot in the correct direction to simulate the action of parallel skiing. The first resilient element is fastened to the carriage at about a mid-point. One end of the first resilient element in the preferred embodiment passes around a roller attached to one of the end brace elements, extends back toward the middle of the rails, and is clamped at a clamp assembly attached to an additional brace element between the rails. The other end of the first resilient element similarly passes around a roller at the opposite end brace element, extends back toward the middle of the rails, and is clamped in a clamp assembly attached to the additional brace element between the rails. This unique arrangement provides additional length for the first resilient element over previous devices, and results in a lower percentage of stretch in operation over the unstretched length, extending the life of the element. The end rollers substantially eliminate wearing friction on the first resilient element.

9 Claims, 16 Drawing Sheets

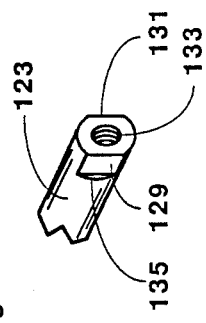
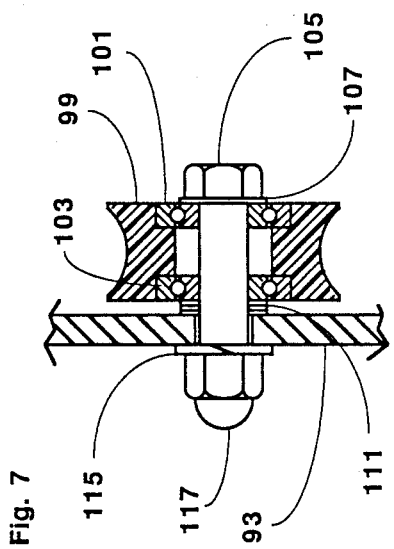

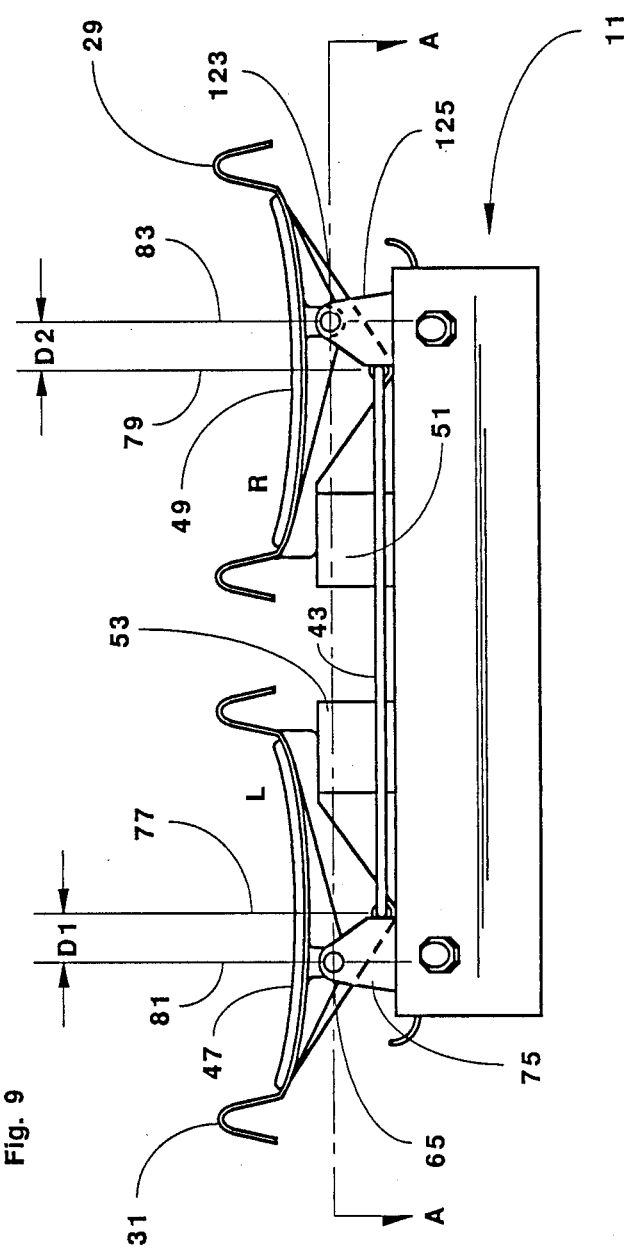

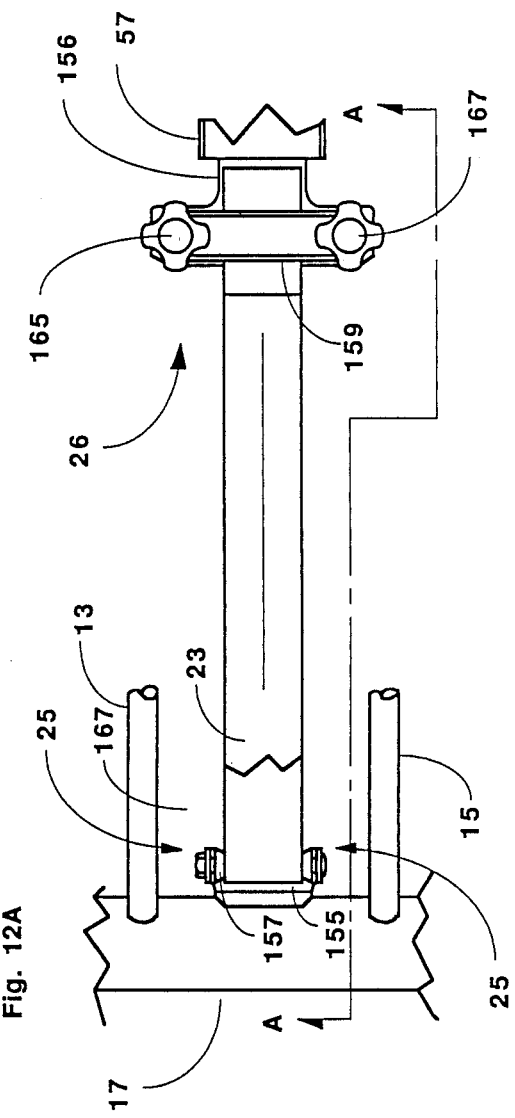
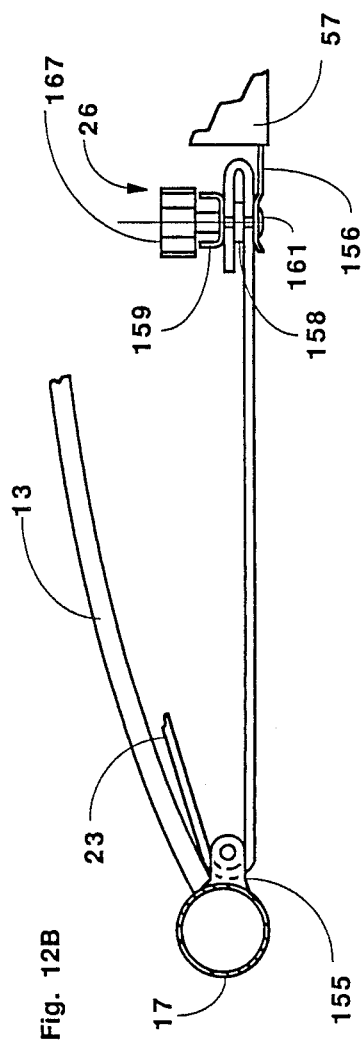
Fig. 12A
Fig. 12B

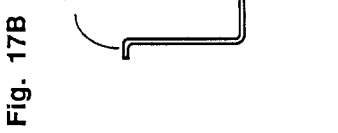
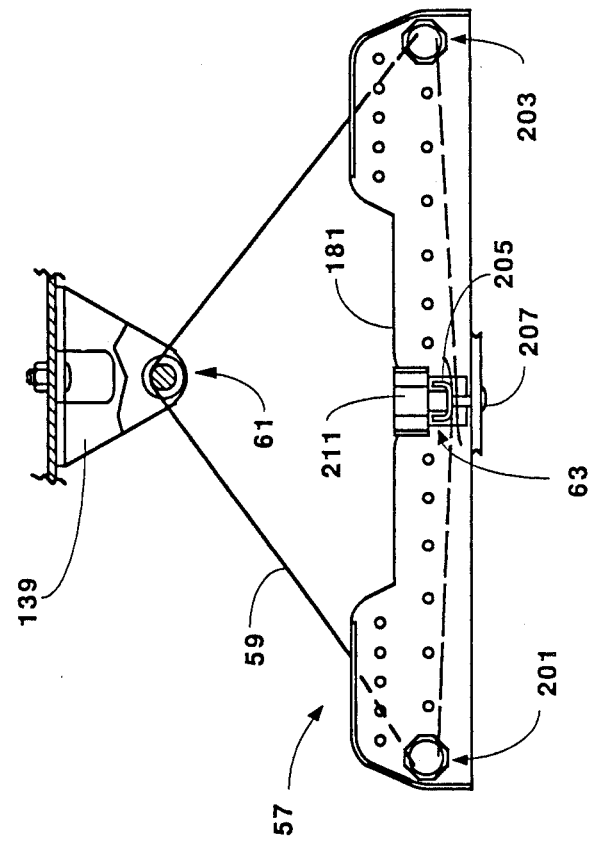
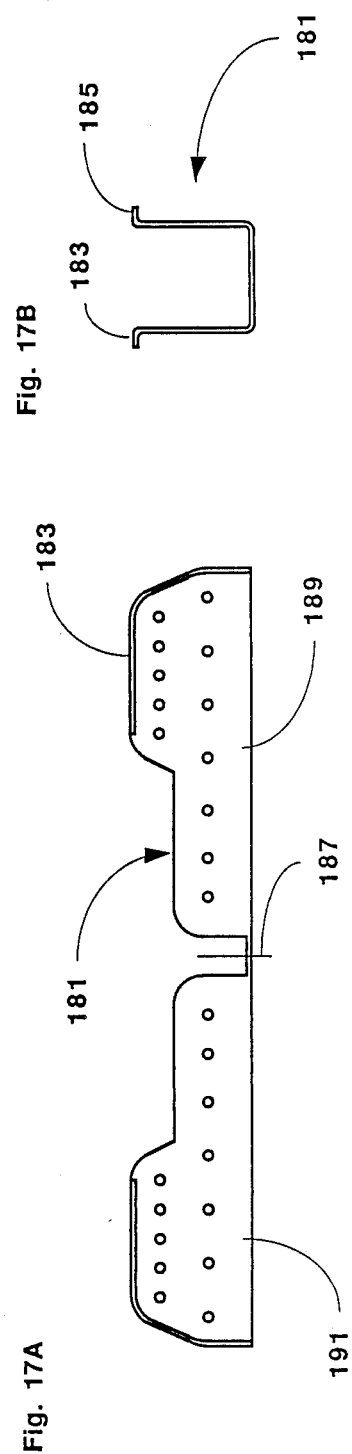

SKI EXERCISING APPARATUS

CROSS-REFERENCE TO RELATED APPLICATIONS

This application is a continuation-in-part of U.S. Pat. application Ser. No. 080,755, entitled SKI EXERCISING APPARATUS, filed Jul. 30, 1987, by R. Joel Loane now issued as U.S. Pat. No. 4,743,014 on May 10, 1988, incorporated herein by reference.

FIELD OF THE INVENTION

This invention relates to exercising apparatus for allowing a user to simulate the motions, exertions and techniques involved in skiing, thereby increasing the user's strength and skill, and more particularly to improvements in such apparatus.

BACKGROUND OF THE INVENTION

Apparatus for use by skiers on which they may simulate the motions, exertions and techniques required in skiing has been built and sold for several years. In particular U.S. Pat. No. 3,524,641 was issued to Robert J. Ossenkop on Aug. 18, 1970, for a device comprising a movable carriage on a set of rails. The carriage of that device is constrained in its movement on the rails by flexible members attached to both the carriage and to transverse members between the rails near each end of the set of rails, and a user can move the carriage from side to side on the rails to simulate the Wedeln or "parallel" technique of skiing.

U.S. Pat. No. 3,547,434 was issued to the same inventor on Dec. 15, 1970. This later referenced patent is for a device similar to the first device, but comprising a number of improvements, such as movable footrests on the carriage whereby a user may simulate turning and edging techniques in addition to parallel skiing; and, in some embodiments may also move the feet relative to one another.

The inventions referenced above each include a safety strap attached to a transverse member between the parallel rails and to the carriage on the rails in addition to the flexible member by which the carriage is constrained to travel on the rails. The purpose of the safety strap is to provide for the situation in which the aforementioned flexible member might rupture on one side of the carriage, providing a sudden force urging the carriage to the side where the flexible member remains unruptured, which sudden force could dislodge a user and perhaps cause serious injury. The safety strap in such instance provides a restoring force toward the center tending to lessen the amplitude of carriage displacement that might otherwise occur.

In the copending parent application, Ser. No. 080,755, an (exerciser) is disclosed having a pair of spaced apart rails, a platform for riding on the the rails, a first resilient element providing a first restoring force on the platform, and a second resilient element providing a second restoring force on the platform. The second resilient element has an adjustment element contacting the second resilient element in at least three points.

In the latter (exerciser) the rails are held in a spaced apart relationship by a brace element in the center, which is fastened to the rails by screw-type fasteners, and by transverse elements fastened at the ends of the rails. The transverse elements at the ends are tubular in form, and the rails pass through openings in the tubular transverse elements, fastening to a bracket internal to each tubular transverse element. This joining arrangement is illustrated by FIG. 1A and FIG. 1B. Rails 301 and 303 pass through holes 305 and 307 respectively into tubular transverse element 309. Inside, the rails are fastened to a bracket 311 by screw fasteners 313 and 315. Rubber-like end caps 317 and 319 close the ends of the tubular transverse element after assembly and act as non-skid pads in contact with the floor in operation. In the copending application, the end caps are of molded rubber-like material, and disk-like pieces carrying designs and lettering are added for identification and esthetic effect. This particular method of joining and spacing the rails has not proved entirely satisfactory in terms of cost and ease of assembly, and in terms of strenght and rigidity of assembly, and the multiple-piece construction of the end caps has also provided to be relatively expensive.

Also in the (exerciser) disclosed in the copending parent application, the first resilient element is fastened to the carriage that rides on the rails, and also is fastened to the tubular transverse elements at each end. The first resilient element is fastened to the carriage by a clamp, and at each end, the resilient element, that in the preferred embodiment has the form of a strap of rubber-like material, passes over, around, and back under the tubular transverse element, terminating at a clamp that is bolted through the tubular transverse element. FIG. 2A and 2B show the arrangement of the bracket and clamp, and the fastening of the first resilient element in the aforementioned application.

As shown by FIGS. 2A and 2B, first resilient element 321 passes over, around, and back under tubular transverse element 309, and then passes between two clamping elements 323 and 325. Bolts 327 and 329 pass through transverse element 309 and also through each of clamping elements 323 and 325. Clamp knobs 331 and 333 engage bolts 327 and 329 and provide pressure to secure the resilient element by friction. This fastening arrangement for the first resilient element at the ends of the exerciser has proven to present a difficulty in that as the carriage moves from one side to the other, urged by a user, stretching the first resilient element, friction over the area of contact where the first resilient element passes over, around and under each of the tubular transverse elements causes wearing effects on the resilient element, resulting in premature failure. Another difficulty is in the length of the portion of the resilient element that stretches when the carriage moves to the side of the exerciser away from the clamp at the end transverse member. In the aforementioned device of the prior art, moving the carriage to one end stretches the resilient element on the opposite side by more than 65 percent.

FIG. 3 is a side view of a pivot platform 335, foot platforms 337 and 339, and associated elements from the aforementioned copending application. Foot pad 337 is pivoted at point 341, and foot pad 339 is pivoted at point 343. The two foot pads are joined by a link 345 so that as they pivot in operation they are constrained to pivot together. The pivot point for each foot pad is substantially at the center, so D1=D2.

The position of the pivot point for each foot pad relative to the width of the foot pad has proven to be very important in operation to simulate parallel skiing technique. In FIG. 3, the letter L near one foot pad indicates the pad where a user would place his or her left foot. The right foot would then be on the other foot pad labeled R. When simulating a right turn on such an apparatus, the weight is shifted to the left foot, and the foot pads must rotate clockwise relative to the plane of FIG. 3. With the weight on the left foot pad, with the pivot in the center of the pad as shown, the force to rotate the foot pads is just as likely to be counter-clockwise as it is to be clockwise around the pivot. Exactly the opposite is true when simulating a left turn, with the same uncertain result with the right foot and the right foot pad. A way to ensure that the foot pads rotate in the proper direction is needed.

FIG. 4 is a partial section through foot pad 339, pivot platform 335 and a carriage 337 that rides on the rails 301 and 303. A pivot shaft 347 passes through flanges of both the pivot platform and the foot pad and the foot pad rotates about the pivot shaft. The pivot shaft passes through bushings such as bushing 349. The shaft is retained by clip retainers such as retainer 351. The pivot platform is mounted to the carriage by screw fasteners. The assembly has a considerable number of parts to be manufactured and assembled, and has proven to be relatively expensive to produce.

Also shown in FIG. 4 is a clamp bar 353 used with two bolts 359 and 361 and two clamp knobs 355 and 357 to clamp resilient element 321 under the carriage. This clamp arrangement is typical of clamps used with the apparatus of the aforementioned copending parent application. The round clamp bar presses on the resilient element in a relatively narrow region and has been shown to cause wear on the resilient element and to also exhibit some problems in strength and rigidity.

Also shown by FIG. 4 is a roller 363 pivoting on a bolt 365 secured by a nut 367. A second resilient element 369 passes over this roller. The roller assembly is typical of several such rollers used in the apparatus. A problem has developed in assembly and operation in that the flanges through which bolt 365 passes and between which roller 363 operates may be drawn in excessively in assembly by excessive tightening of nut 367, restricting the ability of roller 363 to freely rotate and hindering operation of the apparatus. An assembly is needed which is tolerant of assembly pressure.

SUMMARY OF THE INVENTION

In accordance with preferred embodiments of the invention, a device for exercising is provided having at least two parallel rails held in a fixed relationship, preferrably by being welded to brace elements at the ends. A carriage is provided for riding along the rails, and a first resilient element provides a restoring force on the carriage directed toward the center of the rails. Platforms for a user's feet are pivotally attached to the carriage off-center from the centerline of the platforms so that the natural action by a user in shifting weight from one platform to the other platform in operation causes the respective platforms to pivot in the correct direction to simulate the action of parallel skiing. In the preferred embodiment the pivot for each foot platform is a single rod held by a single screw, and the two platforms are constrained to move together by a link between the platforms. Also in the preferred embodiment, one-piece resilient caps are provided at the end brace elements to serve as non-skid contact with the floor.

In the preferred mode, the first resilient element is fastened to the carriage at about a mid-point. One end of the first resilient element passes around a roller attached to one of the end brace elements, extends back toward the middle of the rails, and is clamped at a clamp assembly attached to an additional brace element between the rails. The other end of the first resilient element similarly passes around a roller at the opposite end brace element, extends back toward the middle of the rails, and is clamped in a clamp assembly attached to the additional brace element between the rails. This unique arrangement provides additional length for the first resilient element over previous devices, and results in a lower percentage of stretch in operation over the unstretched length, extending the life of the element. The end rollers substantially eliminate wearing friction on the first resilient element that is typical of previous devices, as well. In addition, the end rollers are mounted on tubular spacers longer than the rollers to avoid interference with the action of the rollers.

Also disclosed in the preferred embodiment is a second resilient element and an adjustment means contacting the second resilient element in at least three points, the three points each formed by a roller, and the rollers mounted on tubular shafts longer than the roller for preventing conflict with the action of the roller.

The improvements disclosed over the previous devices provide for considerably fewer parts, leading to economies in manufacture and advantages in operation, such as increased reliability. The improvements also extend the life of the resilient elements, and provide for a device that more naturally and automatically reproduces the actions and exertions of parallel skiing, such as the proper rotation of the foot platforms as the user urges the carriage from one side to the other.

BRIEF DESCTIPTION OF THE DRAWINGS

FIG. 7 is a cross section of a wheel assembly as used on a carriage according to the preferred embodiment.

FIG. 8 is an end view of a pivot rod used with a foot platform of the preferred embodiment.

FIG. 9 is a side elevation view of a carriage and foot platforms according to the preferred embodiment of the invention.

FIG. 12A is a plan view of a roller and clamp arrangement for attaching a resilient element in the preferred embodiment.

FIG. 12B is a side elevation of FIG. 12A.

FIG. 16 is a side elevation view of an adjustment assembly and a roller bracket used with the second resilient element in the preferred embodiment.

FIG. 17A is a side elevation view of a frame element of the adjustment assembly as used in the preferred embodiment.

FIG. 17B is a end view of FIG. 17A.

DESCRIPTION OF THE PREFERRED EMBODIMENTS

The General Assembly

Figure 5A:
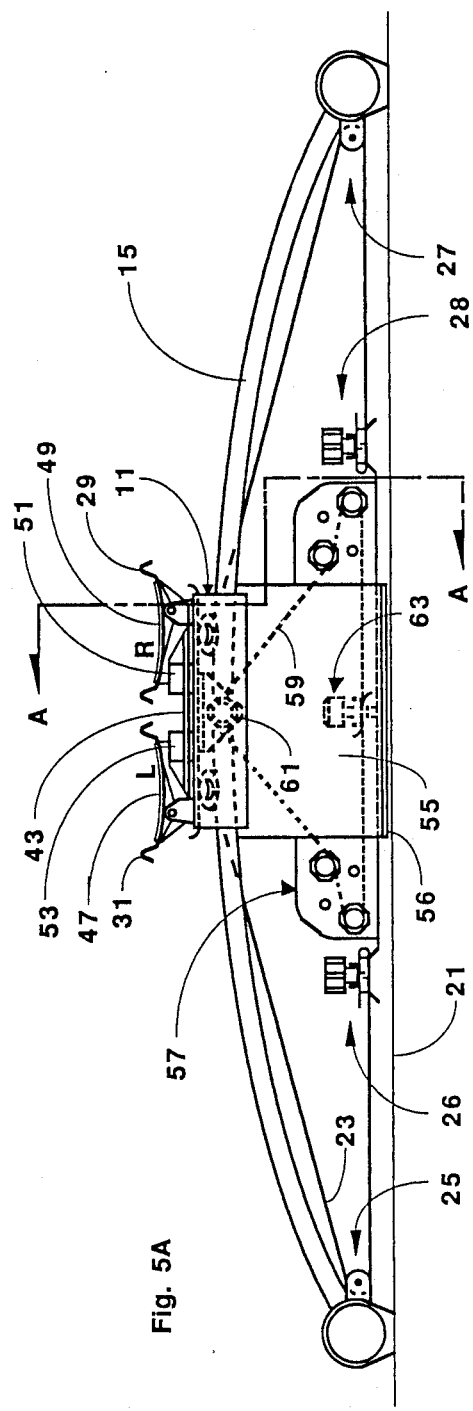
FIG. 5A is an elevation view of an exerciser according to a preferred embodiment of the invention.
Figure 5B:
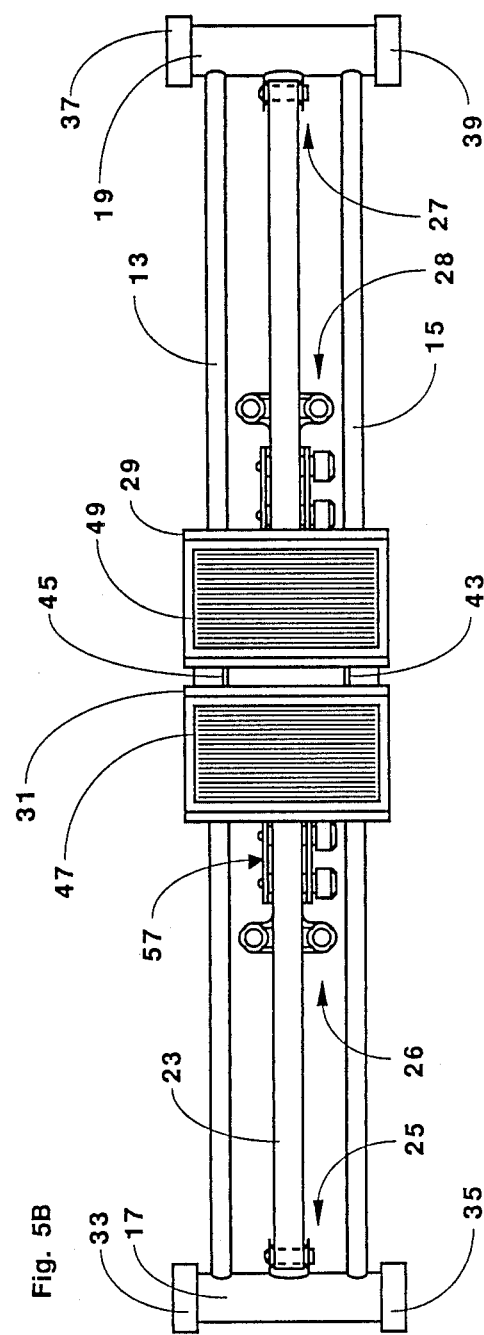
FIG. 5B is an elevation view of the exerciser of FIG. 5A.

FIG. 5A is an elevation view of an exerciser according to the preferred embodiment of the invention. FIG. 5B is a plan view of the exerciser of FIG. 5A. A wheeled carriage 11 rides on a pair of arcuate rails 13 and 15, which are welded to and held parallel by transverse end members 17 and 19. In the preferred embodiment, the rails are about 2.5 cm. diameter in cross section, and the center-to-center spacing between the rails is about 23 cm. The rails are preferably steel tubing with a wall thickness of about 13 gauge, and power coated with a polymer material, which provides exceptional wear resistance and pleasing appearance, although in other embodiments other materials and treatments may be used, as long as the strength of the members is sufficient to stand the expected loading with an adequate safety margin. End members 17 and 19 are also steel tubing, similarly finished as the rails. The diameter of the end members is about 6 cm. The overall width of the assembly is about 32 cm., the overall length in the direction of the arc about 1.6 meters, and the height from floor line 21 to the top of the rails at the highest (center) point is about 15 cm.

A resilient element 23 is fastened to carriage assembly 11 by a clamp assembly (now shown in FIG. 5A or 5B). A length of the resilient element passes around a roller in a roller assembly 25 that is fastened to end transverse member 17, and extends back toward center, where is is secured in a clamp assembly 26. The other end of the same resilient element extends to the opposite side, passes around a roller in a roller assembly 27, then extends back toward center and is secured in a clamp assembly 28. The resilient element is natural gum rubber in the preferred embodiment, but may be other flexible materials in other embodiments such as synthetic rubber. At each end of each of the end members there is a cap, also of rubber in the preferred embodiment, to form the contact of the overall assembly to the floor and to provide a non-skid characteristic on the floor. Caps 33 and 35 are at the ends of end member 17 and caps 37 and 39 are at the ends of end member 19. Caps 33, 35, 37, and 39 are one-piece molded elements in the preferred embodiment, with a decorative logo and message affixed to the outside surface.

Carriage 11 has ball bearing wheels by which it rides on the rail set, which are shown in subsequent drawings, and two foot platforms 29 and 31. The foot platforms are pivoted on flanges of carriage 11, and are connected by links 43 and 45 such that the foot platforms may rock back and forth in the direction of the carriage travel, but are constrained to rock together, and forced to assume a common attitude of tilt. Each foot platform has a non-skid pad added to the upper surface, pad 47 on foot platform 31 and pad 49 on foot platform 29. The amount that the foot platforms may tilt to one side and the force required to accomplished the tilt is controlled in the preferred embodiment by a resilient block 51 on one side and by a similar resilient block 53 on the other side. In the preferred embodiment, the resilient blocks are "closed cell" foam rubber, but may be other flexible material in other embodiments.

There is a U-shaped support member 55 attached to the rails near the center between the end members 17 and 19. This support member has a dual purpose. One purpose is to provide additional strength for the rail assembly. Two vertical portions of support member 55 fit into and fasten to the rails, one portion to rail 13 and the other to rail 15. The strenght of the vertical legs of member 55, which in the preferred embodiment is steel, about 0.3 cm. in wall thickness, helps to hold the spacing between side rails 13 and 15. In addition, the bottom of member 55 when the apparatus is not in use is about 0.6 cm. above the floor line, so that when the apparatus is in use, flexure of the rails will result in the bottom of member 55 contacting the floor and providing sturdy support for the assembly. Member 55 is, like the rails, end members, and other highly visible pieces of the apparatus, powder coated for durability and appearance, although the finish may be different in other embodiments. A non-skid pad 56 similar to pads 47 and 49 is added to the underside of member 55 to make contact with the floor.

Another purpose of the support member is as a frame support for an adjustment assembly 57 which, along with a resilient member 59 and a roller assembly 61 attached to carriage 11, forms an arrangement of elements whereby tension may be adjusted and broadly varied on the carriage without disturbing either of the clamps of assemblies 26 or 28 that anchor the first resilient element, or a clamp assembly 63 which anhcors resilient element 59, which is also a safety strap. This adjustment is done by simply moving pivot rollers from one set of holes to another, as will be subsequently shown in greater detail.

In operation, a user stands on the carriage with one foot on each of the foot platforms. He or she may use poles in one or both hands (not shown) to contact the floor and aid in balance. For the sake of description it will be assumed throughout this specification that a user stands on the platforms in an elevation view facing into the plane of the drawing. The users left foot is then on foot platform 31 and the right foot is on foot platform 29, indicated by L and R in drawing 5A. The user shifts the carriage from side to side to simulate parallel skiing technique. In shifting the carriage to the left, the user's weight is shifted to the left foot, just as in parallel skiing, and the foot platforms need to tilt to the right to simulate a right turn as the resilient elements attached to the carriage slow and stop the carriage and return it toward the center. As the carriage crosses the center, the user's weight is shifted to the right foot, and the foot platforms need to tilt to the left to simulate a left turn as the process is repeated with the carriage traveling to the right of center. Repeated cycles simulate the process of parallel skiing.

The Wheeled Carriage

Figure 6:
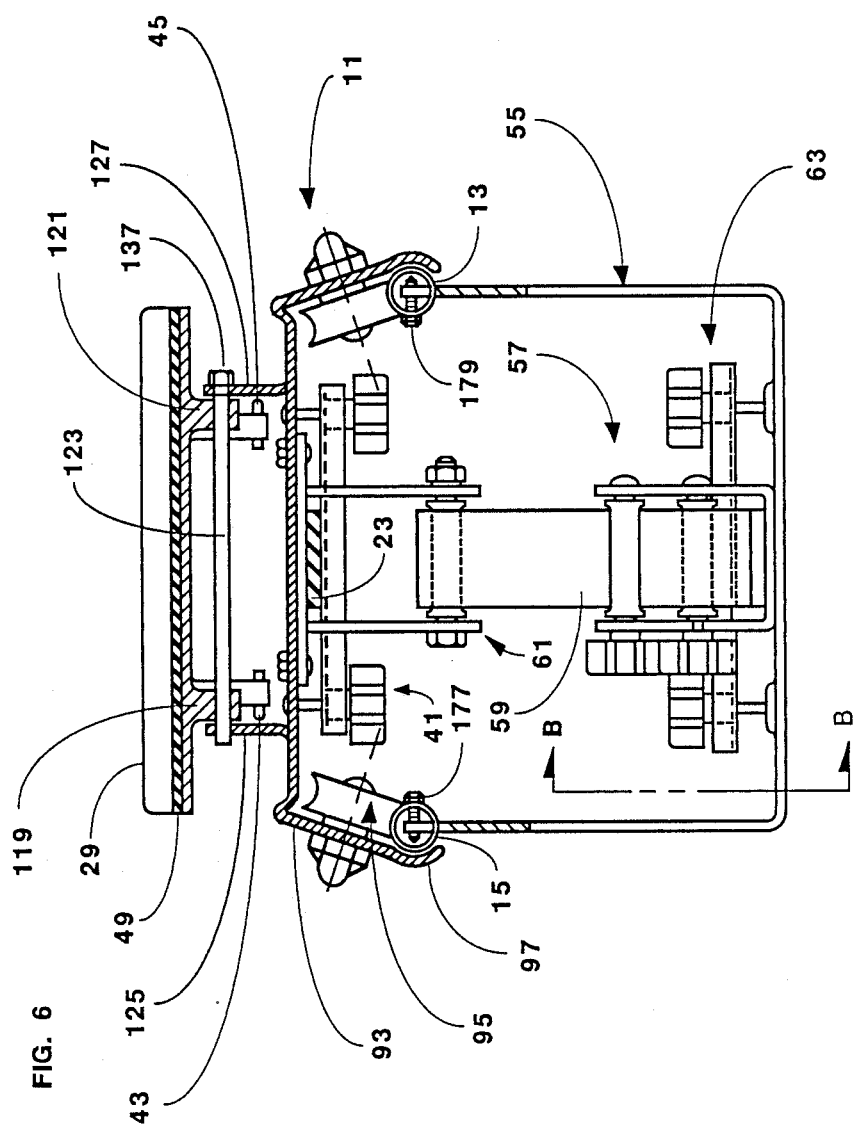
FIG. 6 is a cross section view taken through the exerciser of FIG. 5A and 5B.

FIG. 6 is a section view taken along line A—A of FIG. 5A in the direction of the arrows. The section is through wheeled carriage 11 near the mounting point for two of four wheels upon which the carriage rides on arcuate rails 13 and 15. The carriage has a main body 93 which is sheet metal, and the body has four holes for mounting wheel assemblies such as assembly 95. Body 93 in the preferred embodiment is powder coated for appearance, but other treatments might be suitable in other embodiments. The sides of body 93 are angled at approximately 20 degrees away from the vertical so that the force of the weight of a user of the apparatus, who would be standing on the foot platforms, will be directed slightly outward to each side, thereby increasing the stability of the assembly. The wheel assemblies mount through these angled portions. There is a skirt extension 97 below the point where the wheel assemblies mount that follows the shape of one of the rails. This extension is repeated on the opposite side of the carriage, and serves to guard the area of rolling contact between the wheels and the rails, and to aid in keeping the carriage on the rails in the event of accident or enthusiastic use. The skirts are thus a safety feature.

Each of the four wheel assemblies in the preferred embodiment, of which assembly 95 is representative, is an assembly comprising precision bearings and a wheel, and is a distinct improvement over the prior devices. Illustrated in FIG. 7 is a cross-section of wheel assembly 95. Wheel 99 is machined from a synthetic material formed of extremely long-chain polymers, called UHMW (for ultra high molecular weight). The width of the wheel is about 2 cm., which is about 80% of the diameter of one of the rails. This is considerably wider than wheels of prior devices, and th increased area of contact of a wheel with a rail, wrapping as it does further around a rail, provides a more stable and quieter operation than was before possible. In particular, a larger force in the direction orthogonal to the direction of carriage movement is needed to dislodge the carriage from the rails.

Wheel 99 has machined internal shoulders into which precision ball bearings 101 and 103 are mounted. The bearings are of a higher quality than have heretofore been used with exercisers of this type, and are of a kind commercially available and used with skates and skateboards. A standard hex head shoulder bolt 105 forms the shaft of the wheel and mounts with a flat washer 107 from one side. A stack 111 of the flat washers similar to washer 107 spaces the wheel and bearing assembly away from body 93 of the carriage. Typically three washers are used as spacers. A lock washer 115 and a chrome-plated castle nut 117 fasten the assembly to the carriage body on the side opposite the wheel. In other embodiments it may not be required that the fasteners be chrome plated, as this treatment is for appearance.

It has been found in extensive trails that the improved assembly illustrated provides a safer, quieter, and more durable operation than was heretofore possible with previous exercisers.

Foot Platforms

In the preferred embodiment two individual die cast foot platforms, platform 29 and platform 31, are mounted pivotally to the carriage assembly so that a user may simulate edging technique while using the apparatus. The two platforms are shown mounted side by side in FIG. 5A, and the cross-section view of FIG. 6 shows a section through foot platform 29 as well as carriage 11. Platform 29 is of die cast construction and has a non-skid pad 49 affixed to its upper surface. The pad material is preferably rubber with an embossed, non-skid surface. The pad is fixed to the foot platform by an adhesive in the preferred embodiment. There are other kinds of materials that may be used to accomplish the object and other ways to fix the material to the surface in alternative embodiments, such as with screw fasteners.

Foot platform 29 has depending ears 119 and 121, which are a part of the die casting, and each ear has a hole through which a pivot a rod 123 passes. Carriage body 93 has upward extending flanges 125 and 127, and these flanges also have each a hole through which pivot rod 123 passes. FIG. 8 shows one end of pivot rod 123 on which two flats 129 and 131 are machined. A tapped hole 133, typically #10-32, is also machined in this end of the pivot shaft. The hole in flange 125 for shaft 123 is round, but the hole in flange 127 has two flat sides so that shaft 123 will seat against flange 127 on shoulder 135. The length of flats 129 and 131 is slightly longer than the thickness of the metal of body 93. A screw fastener 137 holds the pivot shaft in place in assembly.

The design of pivot shaft 123 and the mounting holes in flanges 125 and 127 provides a durable and functional pivot with a minimum number of parts and maximizes ease of assembly. Foot pad 31 is mounted to separate flanges of body 93 in a similar manner to that shown for foot pad 29, and with similar parts.

Figure 10:
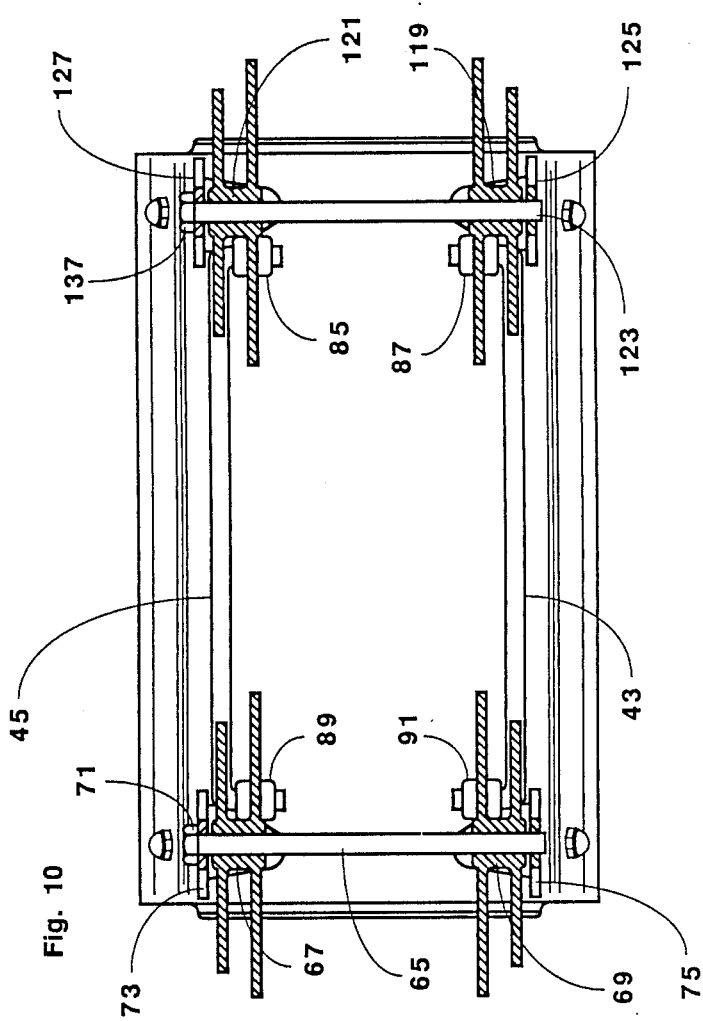
FIG. 10 is a section view of the assembly of FIG. 9.

The foot platforms may rock to a limited degree about the hinged pivots, but they may not rock independently of one another in the preferred embodiment. FIG. 9 is an elevation view of the two foot platforms showing the hinging and other connections in addition detail. FIG. 10 is a section view of this assembly along section line A—A of FIG. 9, and in the direction of the arrows. The section passes through depended ears 119 and 121 of foot platform 29, and through pivot rod 123, but the rod is not shown in section.

FIG. 10 shows a pivot rod 65 for foot platform 31 passing through depending ears 67 and 69, which are a part of die cast foot platform 31. Pivot rod 65 passes through two flanges 73 and 75, which are a part of body 93 of carriage 11, and the rod is held in place by screw fastener 71, forming a pivot for foot platform 31 in the same way that pivot rod 123 forms the pivot for foot platform 29.

Line 77 of FIG. 9 represents the approximate center of foot platform 31 and line 79 the approximate center of platform 29. Line 81 passes through the pivot of platform 31 and line 83 passes through the pivot of platform 29. Dimension D1 and D2 are each, in the preferred embodiment, about 1.5 cm. The offset in each case is to the side away from the center of carriage 11. In operation a user, to simulate a right turn in parallel skiing, will shift the carriage to the left and his weight to his left foot on platform 31. In doing so, the line of action of his weight will fall approximately along line 77, and a rotational moment will be applied clockwise around pivot rod 65, causing the foot platforms to rotate clockwise. As platform 31 rotates under the influence of the user's weight, resilient block 53 will be depressed, limiting the amount of rotation. In simulation of a left turn, shifting the carriage to the right and the weight to the right foot on platform 29, the line of action of the user's weight will fall approximately along line 79 causing the platforms to rotate counterclockwise. The offset is quite important to insure that the rotation of the platforms about their pivots is not in the wrong direction. Without this offset, the platform rotation might very well be in the opposite direction than the direction desired.

In FIG. 10, socket 85 is a part of depending ear 121, socket 87 is a part of depending ear 119, socket 89 is a part of depending ear 67, and socket 91 is a part of depending ear 69. Link 45 engages one end in socket 85 and the other in socket 89. Link 43 engages one end in socket 87 and the other in socket 91. The engagement of the two links in the sockets constrains the two pivot platforms to rock about their respective pivot rods in unison.

Carriage Restraint

As illustrated in FIG. 5A, carriage 11 rolls along rails 13 and 15 and is restrained in that movement both by resilient element 23 and by resilient element 59. Element 23 is captured beneath carriage 11 by a clamp assembly 41 (FIG. 6 and FIGS. 11A and 11B), passes, around a roller of roller assembly 25 at one end of the rail set, and extends to a clamp assembly 26 that is fastened to a framing element assembled to the rail set near the center. Element 23 also passes around a roller of roller assembly 27 at the opposite end of the rail set, and extends to a clamp 28 that is also fastened to the framing element near the center of the rail set. As a user urges the carriage to one side, the full length of the portion of resilient element 23 on the opposite side, between clamp assembly 41 under the carriage and the terminating clamp assembly, either 26 or 28, stretches and applies a force to the carriage opposite the force applied by the user, and tending to return the carriage toward the center. The user oscillates the carriage thusly back-and-forth on the rails simulating parallel skiing. As the user leans and shifts, the foot platforms tilt, simulating the edging effect used in skiing. The relative belt tensions control the effort required and the degree of difficulty, so a user may experience the physical demands just as they would be experienced on a ski slope.

Figures 11A, 11B:
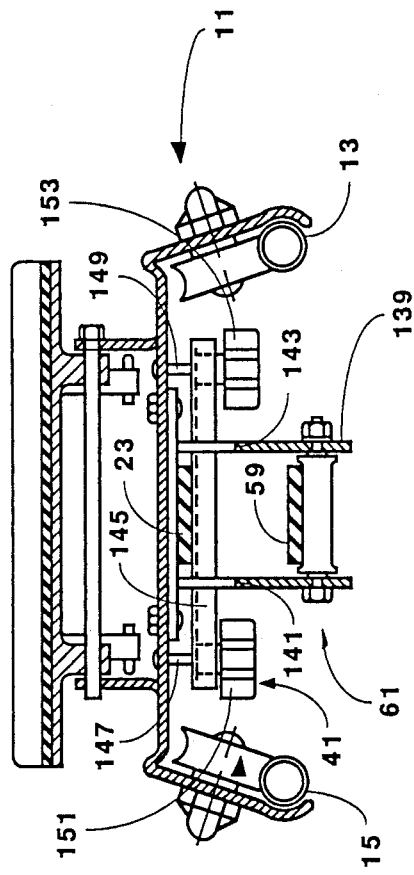
FIG. 11A is a partial section view taken through a carriage and foot platform of the preferred embodiment.
FIG. 11B is a side elevation view of a roller bracket beneath a carriage of the preferred embodiment.

FIG. 11A illustrates clamp assembly 41 and roller assembly 61 under the carriage. FIG. 11B is a side view of the clamp and roller assemblies. Roller bracket 139, which is bolted to carriage body 93, has openings 141 and 143 through which a clamp bar 145 extends. Resilient element 23 passes between the clamp bar and the base of the roller bracket, and the clamp bar has two holes through which bolts 147 and 149 pass. The bolts extend through holes in the carriage with the heads on the upper end, and two plastic knobs 151 and 153 thread onto the bolts just below the clamp bar. The plastic knobs are commercially available hardware items with threaded metal inserts. By rotating the knobs, pressure is applied to the clamp bar, hence to the resilient element, firmly clamping the resilient element between the bar and the bracket base.

FIG. 12A is a plan view of roller assembly 25 and clamp assembly 26, and FIG. 12B is an elevation view taken as section A—A of FIG. 12A. A bracket 155 is welded to end member 17 and elements of the roller assembly are assembled to the bracket. Resilient element 23 passes over and around a roller 157, then extends to clamp assembly 26. A bracket 156 is welded to a frame member of adjustment assembly 57 forming the frame of clamp assembly 26. Resilient element 23 passes between a clamp bar 158 and bracket 156, then reverses and passes back through the clamp assembly between bar 158 and a second clamp bar 159. Bolts 161 and 163 (163 is not shown in FIG. 12A or 12B) pass through bracket 156 and clamp bars 158 and 159, and clamp knobs 165 and 167 are used to apply pressure to the clamp assembly, hence to the resilient element, providing a secure anchor to adjustment assembly 57. Roller assembly 27 and clamp assembly 28 are composed of elements similar to those of roller assembly 25 and clamp assembly 26 respectively, and secures resilient element 23 to end member 19 and back to adjustment assembly 57 at the other end of the apparatus.

Figure 1A:
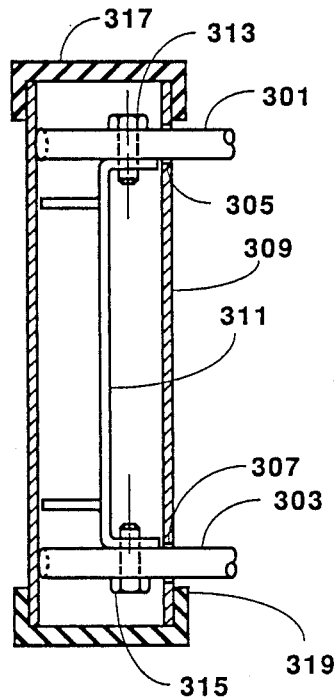
FIG. 1A is a cut-away plan view of an assembly for attaching the rails to an end brace element.
Figure 1B:
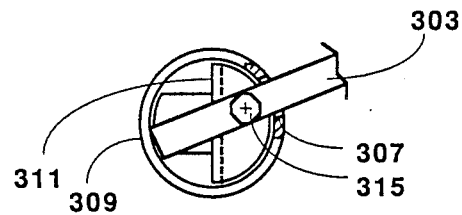
FIG. 1B is an end view of the plan view of FIG. 1A.
Figure 2A:
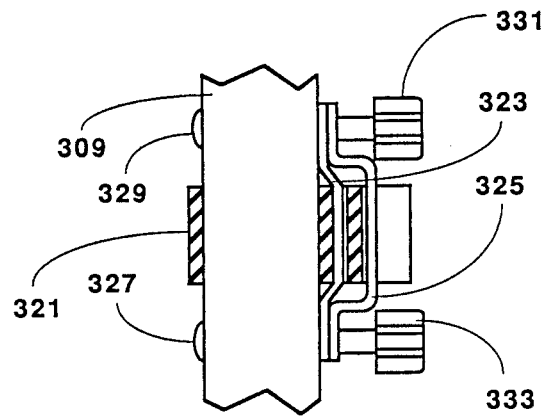
FIG. 2A is a partially cut-away plan view of a clamp arrangement for a resilient element at an end brace element.
Figure 2B:
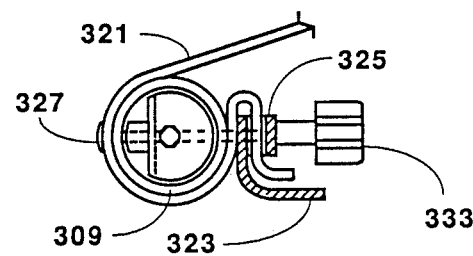
FIG. 2B is an end view of the plan view of FIG. 2A.
Figure 3:
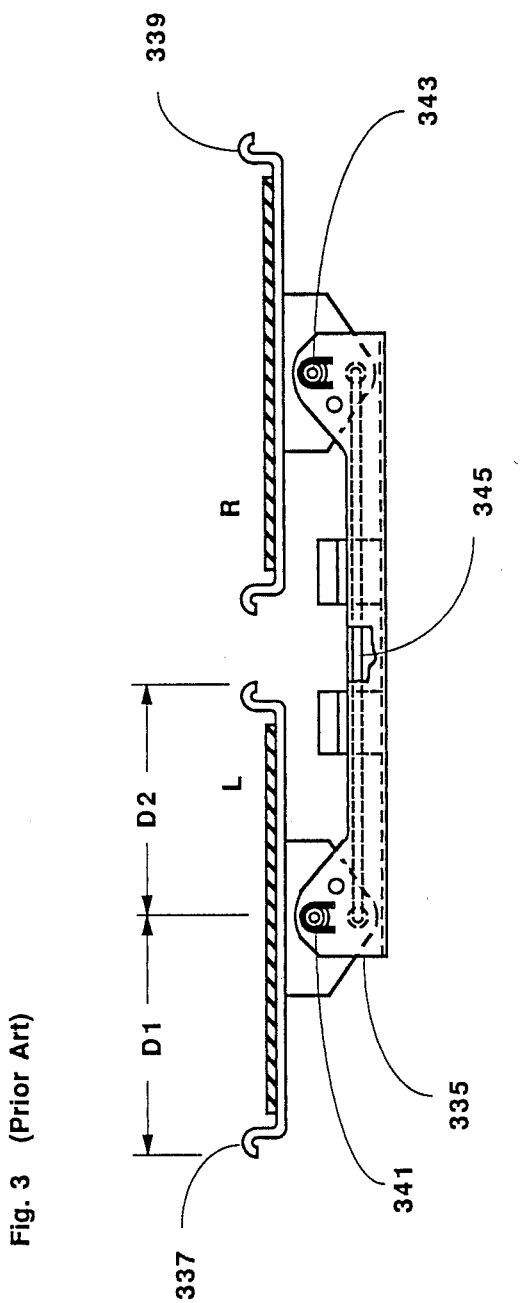
FIG. 3 is an elevation view of a carriage and foot platforms.
Figure 4:
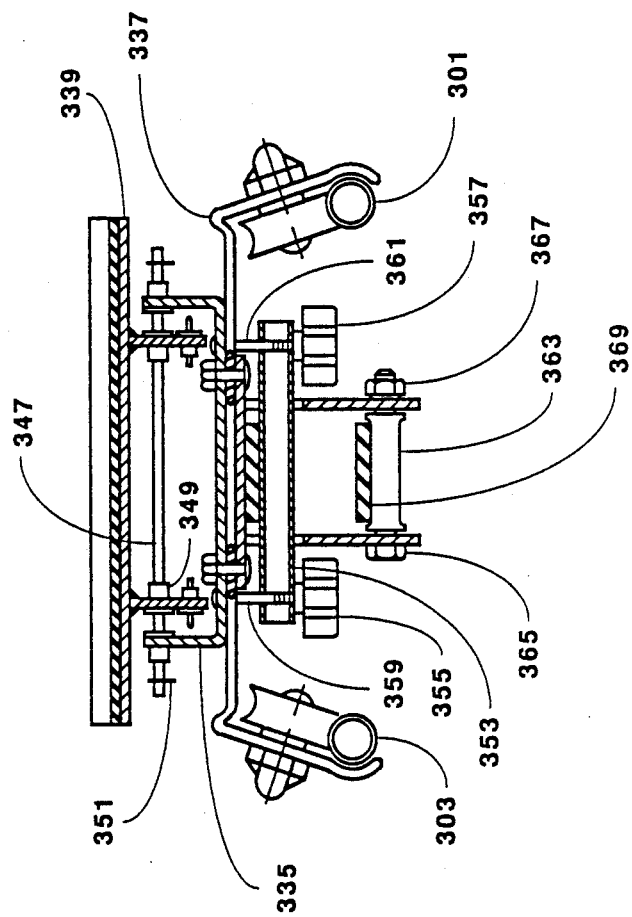
FIG. 4 is a section view through a carriage and foot platform assembly.

The unique design and placement of the roller and clamp assemblies provides additional length for the stretching portions of resilient element 23 over that provided in the prior art, so the relative elongation in operation is about 35 percent rather than more than 65 percent, and rubbing friction where the resilient element passed around the end transverse elements in devices of the prior art such as shown in FIGS. 2A and 2B is eliminated.

Adjustment Assembly

Figure 13:
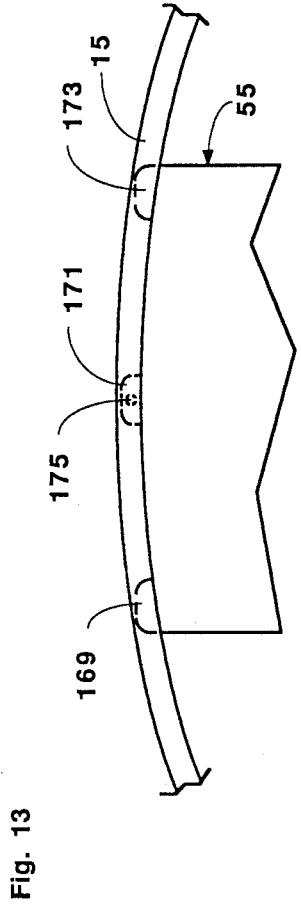
FIG. 13 shows how a third brace element attaches to the rails in the preferred embodiment.

Center support 55 is a U-shaped member fastened below the rail set and to each rail. FIG. 13 shows a central portion of rail 15 from a side view and an upper portion of one vertical leg of support member 55. The vertical leg of member 55 has three ears 169, 171 and 173. Ears 169 and 173 are at each end of the vertical leg, and fit into slots on the underside of rail 15. Central ear 171 fits also into a slot on the underside of rail 15, and has also a hole 175 of about 0.6 cm. diameter. A similar vertical leg with similar ears fits into slots in rail 13. FIG. 6 shows self tapping screws 177 and 179 that pass through holes in rails 13 and 15 to engage the holes in the central ears of the sides of support member 55.

Support member 55, as seen in FIG. 6, helps to space and support the rail set, and also supports adjustment assembly 57 and clamp assembly 63, seen in end view, as well as clamp assemblies 26 and 28.

FIG. 16 is a side elevation view of the adjustment and clamp assembly from the vantage of line B—B of FIG. 6. Clamp assemblies 26 and 28, the brackets for which are welded to the frame of adjustment assembly 57 in the preferred embodiment, are not shown in FIG. 16 or following views, as the purpose of these views is to explain the operation of the adjustment assembly.

FIG. 17A is a side view of a U-shaped member 181 that is the principal frame of the adjustment assembly. Frame 181 is fastened in assembly to support member 55. FIG. 17B is an end view of frame 181. Lips 183 and 185 which are formed at the upper edges of side legs of frame 181 are to present a blunt edge for safety purposes. Similar lips are added to the opposite end of the frame member. Frame 181 is symmetrical about a centerline 187 and there are four upright portions. Portions 189 and 191 of FIG. 17A are mirror image portions, and there are similar portions forming the other side of the frames. There are two horizontal rows of holes in the four upright portions. In portions 189 and 191 the holes are round and each about 0.6 cm diameter. In the similar portions forming the uprights on the other side of the frame the holes are square to fit the under-head of standard stove bolts. The lower row in each portion is an array of seven holes in the preferred embodiment, about 2.9 cm. above the base and spaced about 3.5 cm. apart. The upper row of five holes is about 6 cm. above the base and the holes are spaced about 2 cm. apart. These patterns are mirrored in the other upright portions of the frame member.

Figure 14:
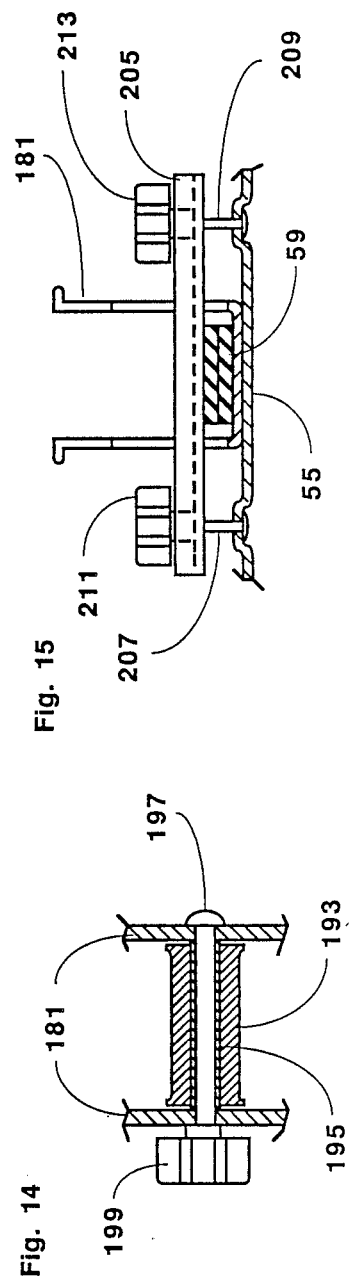
FIG. 14 is a section view through a roller assembly as used several places in the device according to the invention.

Using any hole set consisting of a round hole in one upright portion and the matching square hole in another, across the width of frame 181, a roller assembly may be assembled. FIG. 14 shows such an assembly. A tubular spacer 195 is captured between the sides of frame 181 by a stove bolt 197 that passes through both sides of the frame and the spacer. The square underhead of the bolt fits into the square hole on one side of the frame. A roller 193, preferably of UHMW material and with a central hole, assembles over the tubular spacer and rolls on the spacer. A clamp knob 199, which is similar to knobs 165 and 167, secures the assembly. The use of the spacer allows the roller to freely rotate and prevents the sides of the frame from collapsing against the roller under pressure from the clamp knob. This is an improvement over the prior devices. All of the roller assemblies of the exerciser apparatus are assembled with spacers as shown for the roller assembly of FIG. 14.

In FIG. 16 a roller assembly 201, similar to the assembly of FIG. 14, is assembled to the outermost position of the lower line of seven hole sets at one end of frame member 181. Another roller assembly 203 is assembled to the outermost hole set in the lower row at the opposite end of the frame member. Roller assembly 61 is similar to the roller assemblies illustrated, and is assembled across the sides of roller bracket 139 which is fastened underneath carriage 11. Roller assembly 61 differs only in that a castle nut is used in place of a knob because this assembly is not normally moved for adjustment of forces for the exerciser. The same is true of the roller assemblies of roller and clamp assemblies 25 and 27 at each end of the exerciser.

Figure 15:
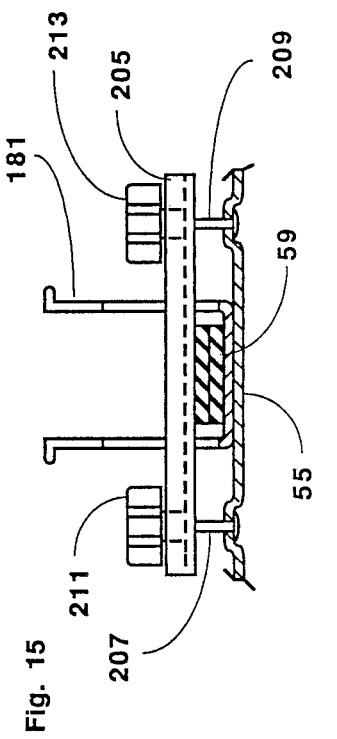
FIG. 15 is a partial section showing a clamp assembly used for a second resilient element in the device of the preferred embodiment.

At the center of adjustment assembly 57 there is a clamp assembly 63 for clamping flexible strap 59 which is similar to the clamp used at the center of roller bracket 139 to clamp resilient member 23. FIG. 15 is a section through this clamp assembly. A clamp bar 205 passes through the center opening of frame 181, and has two holes through which bolts 207 and 209 pass. Clamp knobs 211 and 213 are used with the bolts to apply downward pressure to clamp the ends of resilient member 59 between the clamp bar and the base of frame member 181.

Resilient member 59 is represented in FIG. 16 by a solid and dotted line passing over roller assembly 61 under the carriage, around roller assemblies 201 and 203 near the ends of adjustment assembly 57, with the ends clamped at the center with clamp assembly 63. This is a standard position for the assembly of the exerciser according to the preferred embodiment. Once the two resilient members 23 and 59 of the exerciser are secured; member 23 by assemblies 25 and 27 at the ends and again underneath the carriage; and member 59 by clamp assembly 63 at the center of the adjustment assembly; the clamps need not be loosened again to make force adjustments.

Figure 18:
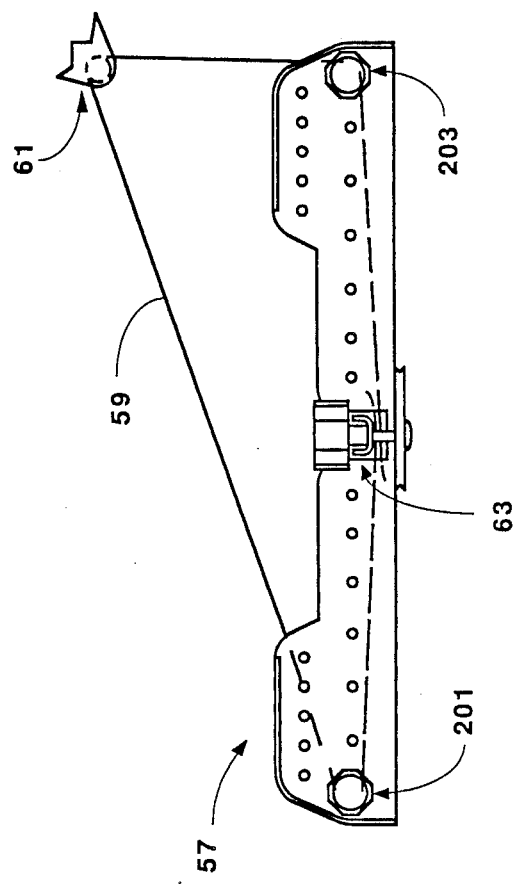
FIG. 18 is an elevation view showing one adjustment of the adjustment assembly of the preferred embodiment.

FIG. 18 shows a situation in which a user has shifted the carriage to one side, so that roller assembly 61 is about overhead one end of adjustment assembly 57. A unique and valuable aspect of the invention is illustrated. The force applied by the stretching of resilient member 59 is a result of the stretch of the entire length of the strap over the three roller assemblies. Force is thus applied more gradually as the carriage moves rather than rather suddenly as is the case with the safety strap in the prior art. Moreover, the sharing of the deformation over a greater length of strap with no localized areas of excessive deformation lowers the average stress level and alleviates fatigue effects, so the straps may be expected to perform longer in service.

Figure 19:
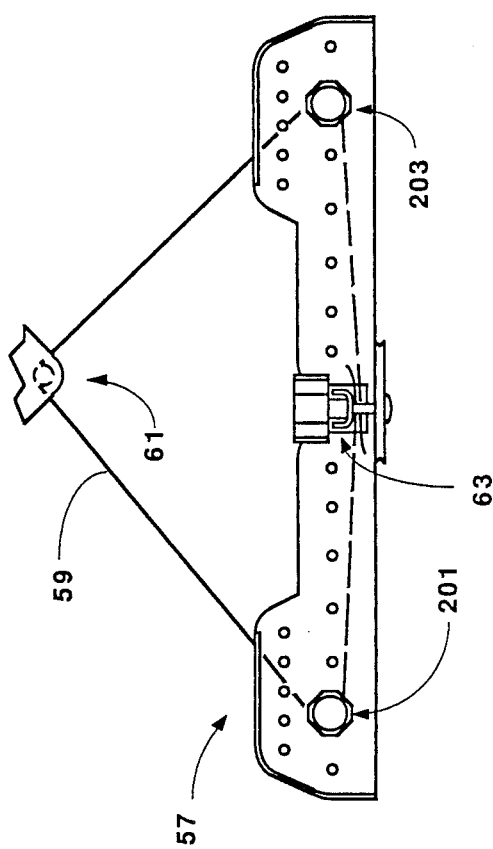
FIG. 19 is an elevation view similar to FIG. 18 showing another adjustment of the adjustment assembly of the preferred embodiment.

From the assembly of FIG. 18, which is a standard starting point, if it is desired that a lower restoring force be applied to return the carriage, as would be the case for a smaller than average user, such as a child, roller assemblies 201 and 203 may be each moved to a position toward the center of the adjustment assembly. By successively moving the roller assemblies one hole spacing toward the center, on each side, the beginning restoring force and the range of force may be reduced in seven steps, corresponding to the seven hole positions in the set. FIG. 19 shows roller assemblies 201 and 203 assembled in the No. 6 position, where the outermost position is considered the No. 7 position.

Figure 20:
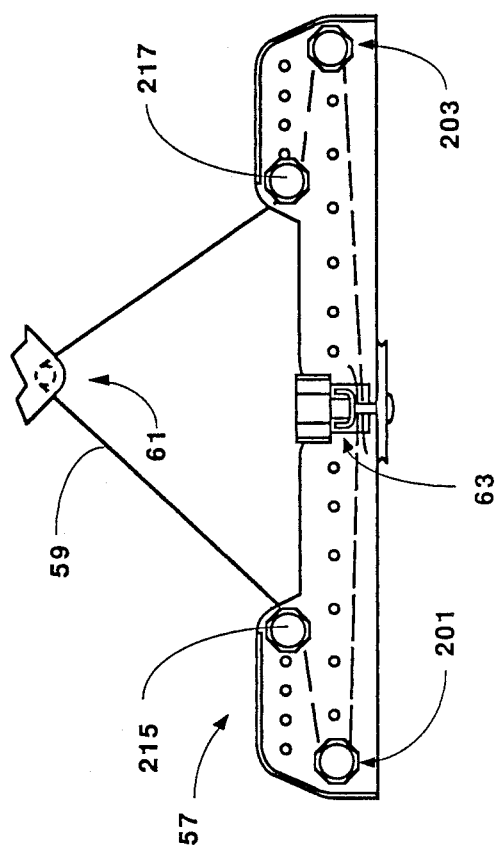
FIG. 20 is an elevation view similar to FIG. 19 showing yet another adjustment of the adjustment assembly of the preferred embodiment.

From the assembly of FIG. 16, if it desired that the restoring force start at a greater force than that for the standard position, which would be the case, for instance, for a larger than normal user, of for a competitor or other agressive skier, who would want a demanding exercise, additional roller assemblies may be added to the top row to increase the initial tension of the resilient element, which will also increase the range of force over which the exerciser will operate. FIG. 20 shows two additional roller assemblies 215 and 217 assembled to the innermost hole positions in the top row of holes in the frame of the adjustment assembly. This is the most agressive adjustment position of the roller assemblies, and will provide a challenge to the skill and endurance of the most agressive skier.

It will be apparent to those skilled in the art that there are many changes that may be made in detail without departing from the spirit and scope of the invention. One may, for example, operate the exerciser with a carriage without foot platforms, therefore without the feature simulating edging technique. The amount that the foot platforms are allowed to tilt may be changed by changing the resilient blocks placed beneath the foot platforms for that purpose. It is quite possible that foot platforms may be installed such that the platforms may swivel instead of tilt, or swivel and tilt at the same time. The material of one or both resilient members may be changed. The tension of the resilient members may be adjusted by adjusting clamps and rollers. The layout of holes in a frame for moving rollers from one position to another to adjust the response of the exercise to a user may be altered in a wide variety of ways without departing from the spirit and scope of the invention. Similarly, instead of two rows of holes in the adjusting frame for moving rollers, there may be only one row of holes. Such modifications are intended to be included within the spirit of the present invention, as limited only by the scope of the following claims.

What is claimed is:

1. A device for exercising comprising:
   at least two rails positioned in a spaced apart parallel relationship;
   brace means for holding said rails in said spaced apart relationship, said brace means comprising a first brace element at one end of said rails, a second brace element at the other end of said rails, and a third brace element attached to said rails between said first brace element and said second brace element;

carriage means for providing a stable riding area for riding along said rails;

first resilient means for providing a restoring force on said carriage means toward the middle of said rails, said first resilient means attached at substantially its midpoint to said carriage means, one end of said first resilient means passing around a first roller means at said first brace element and attaching to said third brace element, the other end of said first resilient means passing around a second roller means at said second brace element and attaching to said third brace element;

second resilient means for providing a second restoring force on said carriage means toward the middle of said rails; and adjustment means for adjusting the magnitude of said second restoring force, said adjustment means contacting said second resilient means at least three point, with a first one of said three points located in a vertical plane on one side of the middle of said rails, with a second one of said three points located in a vertical plane on the other side of the middle of said rails, and with a third one of said three points associated with said carriage means and moving therewith.

2. A device as in claim 1 comprising a first clamping means attached to said third brace element with one end of said first resilient means clamped in said first clamping means and a second clamping means attached to said third brace element with the other end of said first resilient means clamped in said second clamping means such that said first resilient means may be clamped at different points to adjust said restoring force provided by said first resilient means on said carriage means.

3. A device as in claim 1 wherein said adjustment means comprises movement means for moving said first and second points in at least one of a horizontal and a vertical direction, thereby changing the magnitude of the restoring force caused by said second resilient means.

4. A device as in claim 1 comprising platform means attached to said carriage means for placing a user's feet.

5. A device as in claim 4 wherein said platform means comprises a first platform and a second platform, one for each of a user's feet, said first and said second platforms being each pivotally attached to said carriage means such that each may rotate in both directions from the horizontal, with the pivot axis for each said platform being at substantially a right angle to the direction of travel of said carriage means.

6. A device as in claim 5 wherein said first foot platform is attached to said second foot platform such that both foot platforms are constrained to rotate together, maintaining substantially the same angular rotation from the horizontal.

7. A device as in claim 1 wherein said first and said second brace elements are welded to said rails forming a single welded frame structure.

8. A device as in claim 1 comprising a plurality of resilient caps for making non-skid contact with the floor, two such caps affixed to said first brace element and two such caps affixed to said second brace element.

9. A device as in claim 1 wherein said first resilient means is a resilient strap and said first and said second roller means each comprises a first tubular member turning on a second tubular member with said resilient strap passing around said first tubular member, said first tubular member being of greater length than the width of said resilient strap and lesser length than said second tubular member.

* * * * *